United States Patent [19]

Bottesch

[11] Patent Number: 5,323,468
[45] Date of Patent: Jun. 21, 1994

[54] BONE-CONDUCTIVE STEREO HEADPHONES

[76] Inventor: H. Werner Bottesch, Rd. #6, Box 374, Danville, Pa. 17821

[21] Appl. No.: 906,419

[22] Filed: Jun. 30, 1992

[51] Int. Cl.$^5$ ............................................. H04R 25/00
[52] U.S. Cl. ..................................... 381/151; 381/68.3
[58] Field of Search .................... 381/68.3, 68.6, 68.7, 381/188, 151

[56] References Cited

U.S. PATENT DOCUMENTS 4,791,673 12/1988 Schreiber ............................. 381/151
4,887,299 12/1989 Cummins et al. .................... 381/68.4

Primary Examiner—Curtis Kuntz
Assistant Examiner—Sinh Tran
Attorney, Agent, or Firm—Bernard A. Chiama

[57] ABSTRACT

An arrangement was devised for the delivery of stereophonic soundwaves through the mastoid bone structure of the human skull. The system allows for the partial bypassing of the use of the auditory canals, and for the conduction of audio output signals generated in a stereo radio, tape player or other audio device, leaving the auditory canals unobstructed and able to receive airborne sound waves. The system includes one or more accoustical transducers applied to the sides of a person's head adjacent each of his ear canals and in accoustical conduction with the mastoid bone structure thereat. Incoming audio signals to be received through the bone structure are processed in a manner in which these signals are compared to the sonic conductivity data for the bone structure so that selective amplification of the sonic frequency spectrum which are more poorly or slowly conducted through the mastoid bone structure may be enhanced thereby increasing the efficiency of the reception of the incoming audio signals by the person.

10 Claims, 4 Drawing Sheets

BONE-CONDUCTIVE STEREO HEADPHONES

This invention relates to the conduction of selectively amplified sound frequencies through the human mastoid bone structure for the purpose of communicating with the person by way of the mastoid bone structure.

The present invention provides a means for the conduction of soundwaves through the mastoid bones of the human skull for the purpose of allowing the listener to receive those soundwaves while leaving his auditory canals otherwise unobstructed, so that sounds from a person's immediate environment may be normally received. Means are also provided for selectively amplifying those sonic frequencies which do not conduct well through the bone structure.

The system includes a stereophonic radio device, a processor, a means for storing data pertaining to the selected sonic frequencies which are poorly conducted through the human mastoid bone, amplifier/graphic equalizer circuitry and a pair of specially modified sonic transducers fitted with cups which make contact with the external skin covering the mastoid bone structure, and a means for improving the contact between the skin and the sonic transducers. This invention also has application in the fields of military and commercial aviation as well as in the field of audio-based consumer electronics

DESCRIPTION OF THE PREFERRED EMBODIMENT

Figure 1:
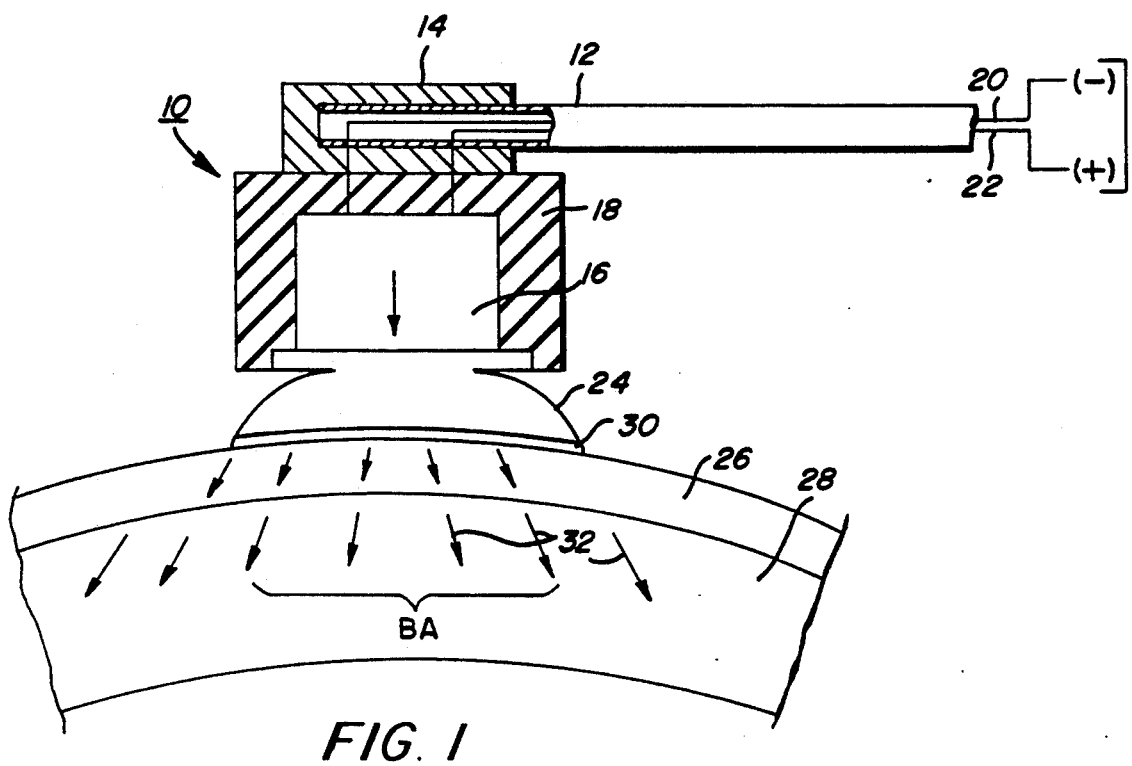
FIG. 1 is a cross-sectional elevational view of a singular bone-conductive headphone unit arranged in accordance with the present invention.

The present invention includes stereo headphones arranged in bone-conductive relationship with a person's mastoid bone structure, and in conjunction with a computerized means for optimizing the transmission of sonic frequencies through the mastoid bone structure.

It is the purpose of the present invention to provide a headphone device which will enable it's user to listen to broadcast, prerecorded or otherwise transmitted audio media without the necessity of the device obstructing the ear canals of the user. The advantages of the present invention over the prior art will become apparent on closer examination of the following disclosure.

Immediately apparent are the safety-related features of the present invention when compared to existing headphone systems. It is the object of the present invention to render the prior art obsolete, in order that public safety be further advanced in relation to the use of headphones. It is well known that many pedestrian injuries and deaths occur annually which are related to the use of conventional headphone technologies during athletic activities such as jogging.

It is obvious that when the ear canals of a user are completely covered by an active pair of conventional headphones, practically all external sounds within that person's immediate environment are obliterated from being heard. Consequently, a person using a conventional headphone system would be unlikely to hear changes in their immediate environment, such as the approach of a motor vehicle during jogging or other activity, and may be more inclined to be struck by that vehicle as a result. The numerous headphone-related pedestrian/vehicle accidents occuring annually bear this contention out. Such injuries and fatalities are needless and would be significantly reduced if the present invention were to achieve widespread use.

Aeronautical applications of the present invention could be equally significant, and would allow, for example, the auditory monitoring of intercom communications and radio transmissions without hindering direct auditory communications between immediately proximate crew members and could also facilitate the wearer's unaided auditory detection of sounds within the cockpit. The failure of the intercom system of an aircraft, for example, would not hinder immediate oral communication amongst crew members if the present invention were in use.

Each individual headphone unit of the present invention comprises a high output accoustical transducer capable of producing sonic frequencies which are within the range of human hearing and which are of sufficient intensity to adequately penetrate the mastoid bone structure over which it is held in place. Each such transducer is attached to a thin leaf spring of conventional material and construction, or other supporting member. The spring or other member is so formed as to hold each transducer against mastoid bone structure with sufficient pressure to sustain adequate contact while not significantly impairing the blood circulation of the skin tissue between the bone structure and the transducer.

The transducer is oriented so as to direct sonic frequencies into the affected bone structure and may be covered with a porous material so as not to obscure perspiration in the area of contact. However, the use of suction cups or other means for maintaining contact between the transducers and the affected skin areas is not precluded from use in the present embodiment and is intended to fall within the scope and intent of the embodiment. Furthermore, the use of a fluid, such as mineral oil, to improve the transfer of sonic frequencies from the transducer to the area of reception, as well as the means for retention of such fluid, is to be included within the scope and intent of the present invention.

FIG. 1 illustrates a cross-sectional view of a singular bone-conductive headphone unit 10 which is shown attached to a portion of a support frame 12 for the headphone unit. In FIGS. 1 and 4-6, a headphone attachment member 14 is shown which may incorporate a means for the adjustment of the headphone to the varying angularity of the mastoid bone structure curvatures of the individual wearer. The unit 10 includes a miniaturized, high output accoustical transducer 16 which is capable of producing audible sound waves and is oriented to direct sound output toward the mastoid bone structure of the wearer. The transducer 16 is encased within a supporting, accoustically-resistant housing 18 which serves to enhance the directing of sound energy toward the mastoid bone structure. Electrically conductive wires 20, 22 connect the transducer to an amplifier means to be described below.

In FIG. 1, a physical sound directing means 24 is shown as integrated with the transducer 16 for conducting the sound waves therefrom through the skin 26 of a wearer and into the mastoid bone structure 28. The means 24 may include but is not limited to the use of a conventional, plyable suction cup to facilitate stabilizing the location of the unit 10 on the user thereof. A film of liquid material 30 such as mineral oil may be utilized to further facilitate the conduction of sound between the unit 10 and the user by replacing the air present between the unit and the skin surface 26 of the user.

Arrows 32 illustrate the approximate direction of travel of sound waves issuing from the transducer 16 and into the bone structure 28. It should be noted that more than one accoustical transducer may be used per each mastoid bone structure and that different areas of the mastoid bone may conduct sonic frequencies with greater or lesser efficiency, depending on such factors as bone density and proximity to the internal auditory organs. In addition, the inherent properties of some sonic frequencies themselves may impose limitations on the degree of their conductivity through the mastoid bone, in general, and through selected sites thereon, in particular.

The following is intended to illustrate an approach to enhancing the perception of sound through the human mastoid bone, thereby further enhancing the listener's perception of bone-conducted sounds.

The frequency range of human hearing can be subdivided into a number of narrower frequency ranges. The more the frequency range of human hearing is subdivided, the narrower will be the frequency range of each of its subdivisions. Within the range of human hearing, certain ranges of sonic frequencies, because of their inherent properties with relation to sonic bone conductivity, are not conducted as well as others are, through the human mastoid bone structure.

Therefore, it is contemplated to further optimize the present invention by applying existing knowledge pertaining to those areas of mastoid bone structure which best conduct designated frequency ranges of sound; by locating individually controlled accoustical transducers over each of these areas; by electronically separating, enhancing and directing those audio signals which normally produce poorly conducted ranges of sonic frequencies to the individually controlled transducers over the areas of the bone structure where frequencies are best received; and by selectively amplifiying the signals producing these frequencies to enhance the reception.

A database representing these ranges of poorly conducted sonic frequencies may be compiled by a processor. This can be accomplished by first converting these known sonic frequencies to analog format, digitizing the analog format, and storing the data derived therefrom in a manner accessible by a processor. Those sonic frequencies which are more readily conducted through the mastoid bone are also digitized, separated, reconverted to analog format without enhancement and are then recombined with the enhanced analog signals prior to their reconversion to sonic output at the transducers.

Figure 2:
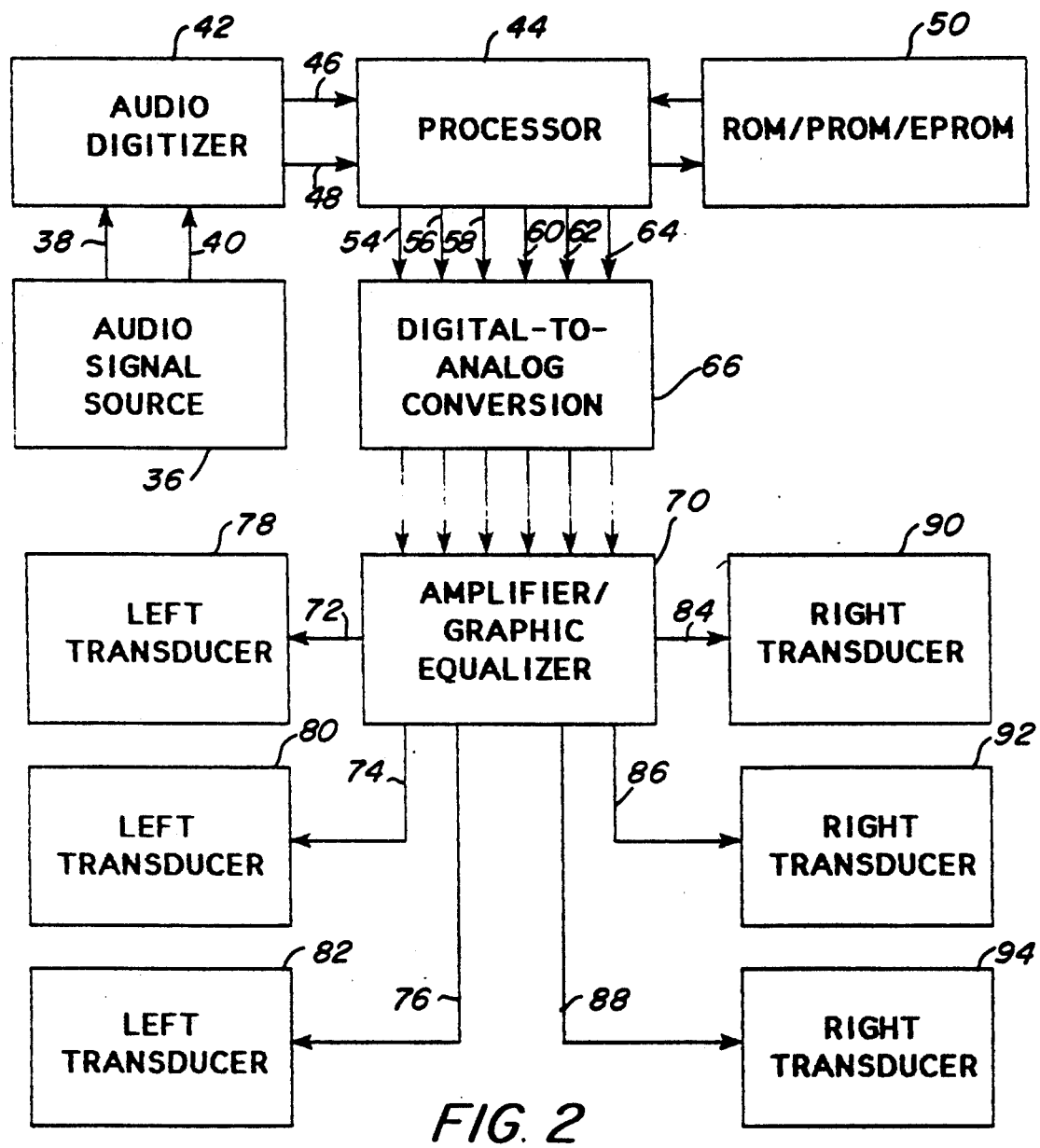
FIG. 2 is a flow diagram illustrating the interactions between the various components of the present invention.

The flow diagram of FIG. 2 illustrates the preferred configuration of components for the present invention. Essentially, stereo audio signals from an analog audio signal source 36 are conducted by conventional means by way of left and right audio channels 38, 40, respectively.

The term "analog audio signals", in the context of this disclosure, refers to those analog signals which are produced by a radio or other such audio signal generating device and which would normally be output by such devices to a conventional loudspeaker circuit but which are instead input to a digitizer for conversion to digital format.

The analog audio signals from the left and right audio channels 38, 40 are digitized by means 42 and the resulting data derived therefrom comprising digitized audio signals, are then inputed to a processor 44 by way of conductive lines 46, 48, for conveying the audio signals from the left and right audio channels 38, 40, respectively. The processor 44 is programmed to constantly analyze these inputs in the following manner.

The aforementioned database, comprised of data representing the poorly conducted sonic frequencies, is stored on a ROM, PROM or EPROM chip 50, or other suitable means for data storage. These data are accessed by the processor 44 and are used by the processor as a source of reference data to which the digitized incoming analog audio signals being input on the lines 46, 48 are continually compared. These sonic frequency data are separated by the processor 44 into groups which abstractly represent specific frequency ranges of the poorly conducted sonic frequencies. The data representing these specific ranges of poorly conducted sonic frequencies are hypothetically referred to as ranges "A", "B" and "C" in the context of the present disclosure.

The processor 44 is programmed to compare the data derived from the incoming analog audio signals from the digitizer 42 to the database of sonic frequency data ranges "A", "B" and "C" (abstractly representing the ranges of poorly conducted sonic frequencies). On the basis of that comparison, the processor 44 is further programmed to identify and separate those portions of the data representing the incoming analog audio signals (which will later be used to reproduce those sonic frequencies which are poorly conducted by the mastoid bone structure) from those which will reproduce sonic frequencies which are not as poorly conducted.

Those data, derived from the incoming audio signals, falling within limits of the sonic frequency data ranges "A", "B" and "C" are thus identified and separated by the processor as a result of this comparison. Once thus separated, these data, representing those portions of the incoming audio signals which produce poorly conducted sonic frequencies can be converted to analog format and be selectively and separately amplified (therewith avoiding the collective and otherwise unenhanced amplification of all of the digitized incoming analog audio signals), thereby enhancing the listener's perception of those sonic frequencies which are normally poorly conducted through the mastoid bone structure.

The processor 44 will also have access to a program which is written for the purpose of enabling the processor to organize the digitized and separated audio frequencies data for eventual output to designated pairs of sonic transducers once the data has been reconverted to analog format. Thus, the data for sonic frequency data ranges "A", "B" and "C", for example, can be assigned for eventual output to sonic transducers pairs, as will be described below.

The data representing those portions of the incoming analog audio signals which produce poorly conducted sonic frequencies can be modified by a number of methods, in order to increase the listener's perception of the sounds which they represent. For example, these separated frequencies data can be reconverted to analog format, apart from the remaining audio frequencies of the spectrum, and then separately conducted to an amplifier circuit and amplified to a pre-set level of gain, and recombined with the reconverted remaining(unenhanced) audio frequencies data, or; the gain of these separated audio frequencies data may be digitally enhanced by the procesor prior to their digit-to-analog reconversion along with the unenhanced audio frequencies data.

Once this selective amplification is accomplished, the selectively amplified analog signals can be conducted to a single pair of left and right sonic transducers, or be selectively conducted with respect to the frequency ranges "A", "B", "C", to corresponding pairs of left and right sonic transducers located at sites of frequency-specific sonic conduction over the left and right mastoid bone structures, thereby further increasing the perceptible effects of the amplification. In addition, the inclusion of conventional graphic equalizer circuitry in conjunction with the amplifier circuit will further enhance the listener's ability to control their perception of the sound frequencies reproduced through this system.

Once the audio frequency data have been separated into the ranges "A", "B" and "C" for each of the respective audio channels, the processor 44 outputs these data as follows: by way of conductors 54, 56 and 58, for the left audio channel, whereby conductor 54 serves to transmit audio frequency data falling within the data range "A", conductor 56 serves to transmit audio frequency data falling within the range "B", and conductor 58 serves to transmit audio frequency data falling within the range "C"; and by way of conductors 60, 62 and 64, for the right audio channel, whereby conductor 60 serves to transmit audio frequency data falling within the range "A", conductor 62 serves to transmit audio frequency data falling within the data range "B", and conductor 64 serves to transmit audio frequency data falling within the data range "C".

The data comprising audio frequencies data which have fallen within the individual data ranges of poorly conducted sonic frequencies are carried from the procesor 44 to a digital-to-analog conversion device 66 by way of conductors 54, 56, 58 of the left audio channel and by way of conductors 60, 62, 64 of the right audio channel, and are therein converted from digital format to analog audio signals. These analog audio signals are conducted on the lines 55, 57, 59, and 61, 63, 65 and are then individually and selectively amplified by an amplifier/graphic equalizer 70 and are further transmotted by conductors 72, 74, 76 to left accoustical transducers 78, 80, 82, respectively, and by conductors 84, 86 and 88 to right accoustical transducers 90, 92 and 94, respectively.

It should be noted that the degree of amplification of the audio signals input on lines 55, 57, 59, 61, 63, 65 is to be individually adjusted and set in accordance with existing information pertaining to the sonic conductivity of the various sonic conduction sites of the mastoid bone, so as to optimize the the conduction of poorly conducted sounds through each such conduction site of each of the mastoid bones by selectively increasing the gain of the poorly conducted sonic frequencies.

For example, if mastoid bone site BA, as shown in FIG. 1, underlying the accoustical transducers 80, 92, requires a certain degree of audio signal amplification for successful penetration and perception of sound by the wearer of the device, this degree of amplification is preset, using means well known in the art. In addition, circuitry, not illustrated but included, will allow the wearer of the device to increase the gain or volume of all channels according to the individual user's audio perception.

In addition, a feature employing the graphic equalizer circuitry 70 is included to further enhance the fine tuning of audio perception by the wearer of the device. The graphic equalizer circuitry may be configured to control the overall output of the left and right audio channels, or it may be configured to separately control individual sub-channels, or both. It should also be understood that the invention shall not be limited to the use of only three sonic frequency data ranges and that the complete spectrum of such ranges may be subdivided into any number of such sonic frequency data ranges.

The means 42 for the conversion of audio signals comprising an analog format to signals comprising a digital format, the means 66 for the reconversion of signals comprising a digital format to audio signals comprising an analog format, as well as the means for amplification of such audio signals are defined in the prior art and do not, per se, constitute a part of the present invention. However, it is to be understood that the application of such means to the present invention is herein acknowledged as inventive and is claimed as such.

Figure 3:
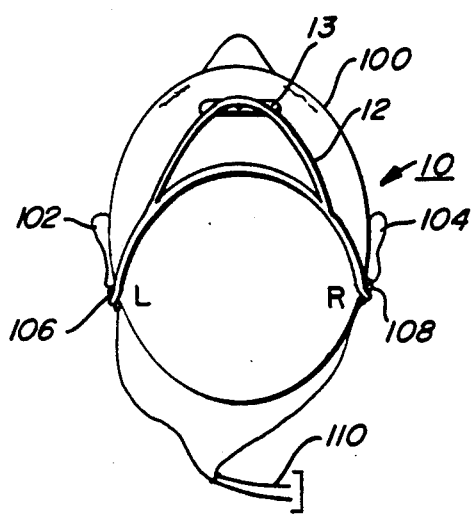
FIG. 3 is a plan view of a person's head and illustrates possible locations of accoustical transducers utilized in the present invention in relation to the bone structures behind a wearer's ears, as well as the placement of components of a proposed means for the support of the transducer;.

In the plan view of FIG. 3, the numeral 100 denotes the head of a human person wearing the bone-conductive headphone unit 10 adjacent each of the external ears 102, 104 of the person and having the support frame 12 with its frontal support pad 13 resting high upon the wearer's forehead. The frame 12 may assume a number of possible headphone support configurations, but preferrably, the support frame includes strips of spring steel, or other suitable material which are formed and joined as shown. At each of locations 106, 108, at least one of the accoustical transducers is shown positioned in relation to the left and right mastoid bone structure of the wearer against which the transducers are placed. Conductors 110 of a wiring circuit are arranged for the conduction of stereo signals from the amplifier 70 to these transducers.

Figure 4:
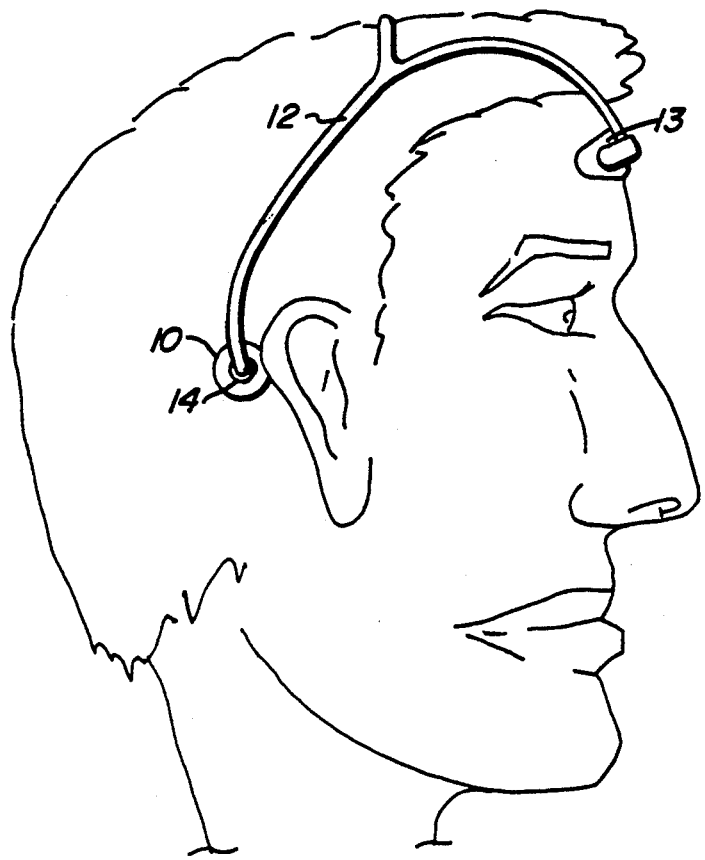
FIG. 4 is a side view of the right side of a person's head and indicates one of a number of possible locations for a singular right-channel accoustical transducer headphone unit in relation to the bone structure behind the wearer's right ear, as well as the placement of components of a proposed supporting means for the transducer.

FIG. 4 illustrates the right side of a person's head and indicates one of a number of possible locations for a singular right channel bone-conductive headphone 10 in relation to the bone structures behind the wearer's ears. The headphone 10 is attached to the support frame 12 by the headphone attachment member 14. The frontal support pad is shown resting high on the wearer's forehead and is attached to the headphone support frame.

Figure 5:
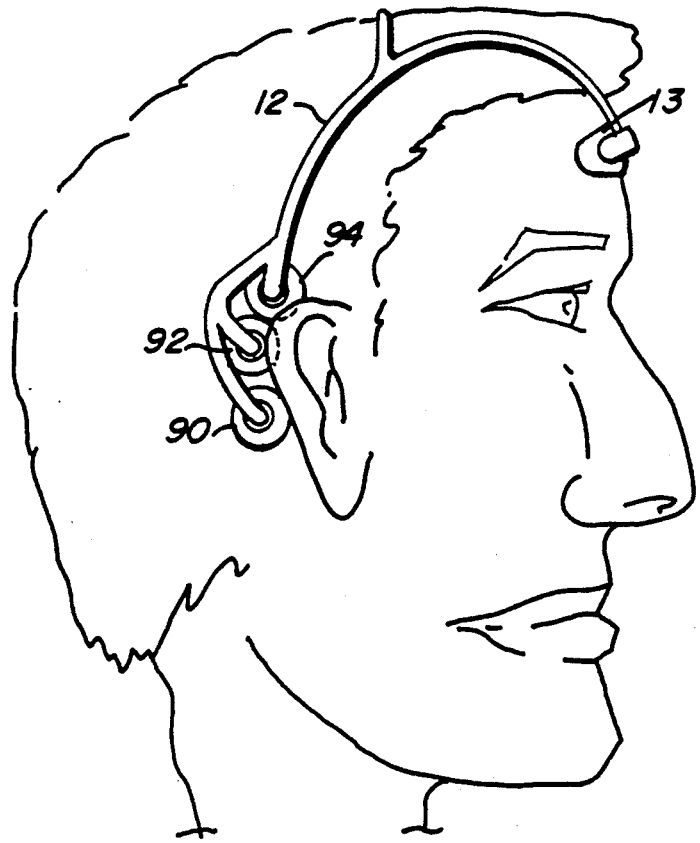
FIGS. 5 and 6 are similar to FIG. 4 and indicate multiple headphone units and an accoustically resistant support housing for the multiple units, respectfully.

FIG. 5 illustrates the right side of a person's head and indicates possible locations for multiple right channel headphone units 90, 92, and 94 (as indicated in FIG. 2) in relation to the bone structures behind and in proximity to the wearer's right ear. The headphone units 90, 92 and 94 are commonly attached to support frame 12 by means similar to that shown in FIG. 4.

Figure 6:
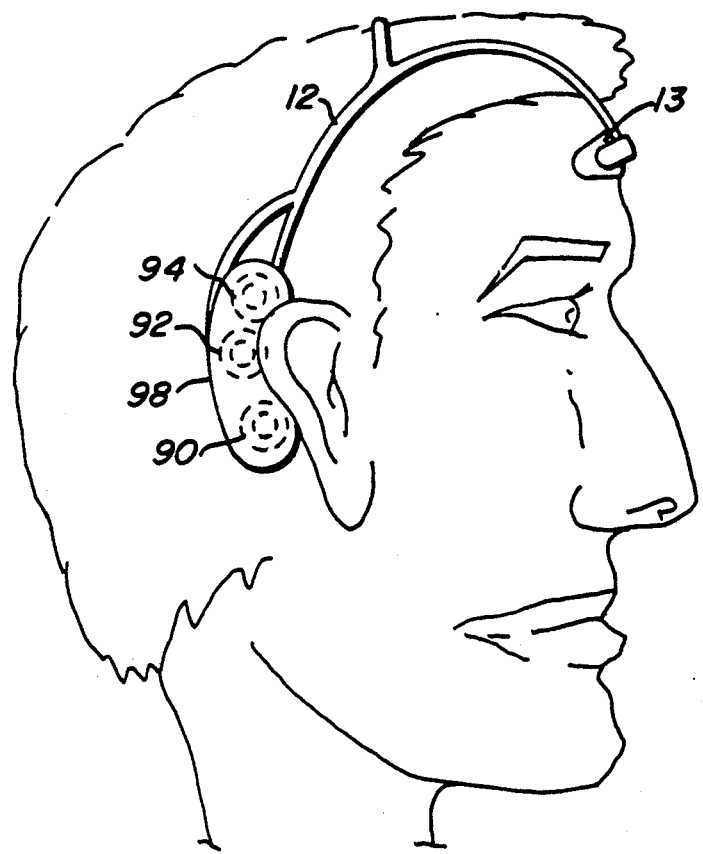

FIG. 6 illustrates the right side of a person's head and indicates a proposed location of an accoustical resistant support housing 98 for the multiple right channel headphone units 90, 92 and 94 (as indicated in FIGS. 2 and 5), also shown in relation to the bone structures behind and in proximity to the wearer's right ear. The support housing 98 is attached to support frame 12, with said headphone units individually articulating within the housing, thereby permitting each of them to individually conform to the angularity of the wearer's skull bone structures.

In an example arrangement, it will be assumed that the human ear is capable of hearing sounds between 20 Hz to 20,000 Hx, and that the major ranges "A", "B" and "C" for the sonic conductivity data ranges would be assigned the major frequency ranges of 20 Hz to 3,000 Hz, and 3,000 Hz to 10,000 Hz, respectively. In this example, it will also be assumed that the mastoid bone structure is such that it responds poorly to the frequency range of 10,000 Hz to 20,000 Hz. In this event, the fidelity of sound reception for the full spectrum of sound in the 20 Hz to 20,000 Hz range is relatively poor, since high fidelity is lacking in one of the major ranges.

The present invention has been devised so that the full spectrum of sonic signals is compared to preset data corresponding to the sonic conductivity capability exhibited by the mastoid bone structure in terms of sonic conductivity data ranges. That range of audio signals within the spectrum which produces poor conductivity effects by the mastoid bone structure is separated from the other ranges and enhanced as by amplification and fine tuning so as to be more effective upon the bone structure. The enhanced signal range is recombined with the unenhanced signal ranges and transmitted to the transducers thereby enhancing the fidelity of sound reception.

From the foregoing, it will be appreciated that the present invention is devised whereby a person may receive audio signals such as those produced by radio, or from tapes, or from various forms of intercom systems without the need for the use of his ear canals. While in use, the present invention allows the unobstructed use of the user's ears to pick up sounds or voices from his surrounding environment in the event some important or dangerous, as well as, informative situation is at or near at hand. The inventive arrangement does not interfere with the normal reception of sounds, but rather complements such reception in that two or more sources and transmissions of information may be received simultaneously, either as separate communications, or as integrated communications.

What is claimed is:

1. A communication system for transmitting incoming analog audio signals to a human person through the mastoid bone structure adjacent the ear canals of the person by utilizing sonic frequency conductivity data ranges of the mastoid bone structure, comprising: at least one accoustical transducer positioned adjacent each ear canal of the person in sound transmitting conduction with a predetermined site on the mastoid bone structure, said transducers being adapted to transmit accoustical signals to its associated bone structure site in response to signals indicative of a predetermined audio frequency data range, means for storing the sonic frequency conductivity data ranges of said sites of the mastoid bone structure, means for comparing the stored sonic frequency conductivity data ranges with the incoming analog audio signals and for producing said signals indicative of said predetermined audio frequency data range corresponding to one of the sonic frequency conductivity data ranges, and means for transmitting said signals indicative of said predetermined audio frequency data range to said transducers thereby effecting the transmission of the incoming audio audio signals to the human person.

2. The communication system as defined in claim 1 including means for converting the incoming analog audio signals into digital format prior to being transmitted to said means for comparing and producing said signals indicative of said predetermined audio frequency data range.

3. The communication system as defined in claim 1 wherein said signals indicative of said audio frequency data range are produced in the digital format, are converted to the analog format, and are selectively amplified in accordance with the conductivity ability of the bone structure site before being transmitted to said transducers.

4. The communication system as defined in claim 1 including paths of transmission for the incoming audio signals to the respective transducers, said paths being arranged by way of separate communication channels thereby effecting stereo reception for said transducers.

5. The communication system as defined in claim 2 wherein said signals indicative of said predetermined audio frequency data range are produced in the digital format, and including means for converting said signals indicative of said audio frequency data range to the analog format.

6. A communication system for transmitting incoming, analog audio signals to a human person through the mastoid bone structure of the person by utilizing sonic frequency conductivity data ranges of the mastoid bone structure, comprising: at least one accoustical transducer positioned adjacent each ear canal of the person and in sound transmitting conduction with a predetermined site on the mastoid bone structure, means for storing said sonic frequency conductivity data ranges of the sites of the mastoid bone structure, said transducers being adapted to transmit accoustical signals to its associated site of the bone structure in response to signals indicative of a predetermined range of a plurality of audio frequency data ranges applied thereto, means for comparing said stored sonic frequency conductivity data ranges with the incoming audio signals, for separating the data representing those audio signals which fall within said predetermined range of said plurality of audio frequency data ranges, and for producing sonic signals indicative of said predetermined range of said plurality of audio frequency data ranges corresponding to one of said sonic frequency conductivity ranges, and means for transmitting said sonic signals to said transducers indicative of the incoming audio signals.

7. The communication system defined in claim 6 including means for selectively amplifying said sonic signals indicative of said predetermined range of said plurality of audio frequency data ranges.

8. The communication system as defined in claim 6 wherein a plurality of accoustical transducers are positioned adjacent each each and each of said transducers is associated with one of said sonic conductivity data ranges, respectively.

9. The communication system as defined in claim 6 including means for recombing said sonic signals with other ranges of said plurality of audio frequency data ranges prior to the transmitting of said sonic signals to said transducers.

10. A method for providing a human person with the reception of stereo audio signals other than through the ear canals of the person, comprising:

positioning an accoustical transducer in sound conduction relationship to the mastoid bone structure on both side of the head of the person, comparing the stereo audio signals with a plurality of sonic frequency conductivity data ranges of the mastoid bone structure, separating the data representing those signals which fall within a predetermined range of said plurality of sonic frequency conductivity data ranges;

producing sonic signals indicative of said signals which fall within said predetermined range of said plurality of said sonic frequency conductivity data ranges and which correspond to one of said predetermined range of said plurality of sonic frequency conductivity data ranges, and transmitting said sonic signals indicative of said predetermined range of said plurality of sonic frequency conductivity data ranges to said transducers.

* * * * *